US010232081B2

(12) United States Patent
Rotmans et al.

(10) Patent No.: US 10,232,081 B2
(45) Date of Patent: Mar. 19, 2019

(54) IN SITU TISSUE ENGINEERING

(71) Applicants: Academisch Ziekenhuis Leiden, Leiden (NL); Xeltis B.V., Eindhoven (NL); Universiteit Maastricht, Maastricht (NL)

(72) Inventors: Joris Ivo Rotmans, Leiden (NL); Tonia Caroline Rothuizen, Leiden (NL); Lorenzo Moroni, Leiden (NL); Clemens Antoni Van Blitterswijk, Leiden (NL); Febriyani Fiain Rochel Damanik, Leiden (NL); Tom Lavrijsen, Eindhoven (NL); Martijn Antonius Johannes Cox, Eindhoven (NL); Antonius Johannes Rabelink, Leiden (NL)

(73) Assignees: Academisch Ziekenhuis Leiden, Leiden (NL); Xeltis B.V., Eindhoven (NL); Universiteit Maastricht, Maastricht (NL)

( * ) Notice: Subject to any disclaimer, the term of this patent is extended or adjusted under 35 U.S.C. 154(b) by 0 days.

(21) Appl. No.: 15/318,426

(22) PCT Filed: Jun. 16, 2015

(86) PCT No.: PCT/NL2015/050442
§ 371 (c)(1),
(2) Date: Dec. 13, 2016

(87) PCT Pub. No.: WO2015/194950
PCT Pub. Date: Dec. 23, 2015

(65) Prior Publication Data
US 2017/0128623 A1 May 11, 2017

(30) Foreign Application Priority Data
Jun. 17, 2014 (NL) .................................. 2013016

(51) Int. Cl.
*A61L 27/34* (2006.01)
*A61L 27/54* (2006.01)
(Continued)

(52) U.S. Cl.
CPC .............. *A61L 27/34* (2013.01); *A61L 27/18* (2013.01); *A61L 27/36* (2013.01); *A61L 27/507* (2013.01);
(Continued)

(58) Field of Classification Search
CPC .......... A61L 27/34; A61L 27/18; A61L 27/56; A61L 27/58; A61L 27/54; A61L 2400/12; A61L 2430/34
See application file for complete search history.

(56) References Cited

U.S. PATENT DOCUMENTS

| 4,319,363 A | 3/1982 | Ketharanathan |
| 2010/0016989 A1* | 1/2010 | Lyngstadaas ............. A61F 2/28 623/23.72 |

(Continued)

FOREIGN PATENT DOCUMENTS

| JP | 2004-261260 A | 9/2004 |
| JP | 2006141681 A | 6/2006 |

(Continued)

OTHER PUBLICATIONS

Osamu Sakai et al: "Faster and Stronger Vascular "Biotube" graft fabrication in vivo using a novel nicotine-containing mold", Journal of Biomedical Materials Research Part B: Applied Biomaterials, vol. 90B, No. 1, Dec. 23, 2008 (Dec. 23, 2008), pp. 412-420, XP55208704, ISSN: 1552-4973, DOI: 10. 102/jbm.b 31300.

(Continued)

*Primary Examiner* — Christine H Matthews
*Assistant Examiner* — Joshua D Lannu
(74) *Attorney, Agent, or Firm* — Hoffmann & Baron, LLP

(57) ABSTRACT

The present disclosure relates to in situ tissue engineering, more specifically in situ vascular tissue engineering with the (Continued)

aim of providing a tissue structure which can be used e.g. as a substitute blood vessel or as a blood vessel functioning as cannulation site in hemodialysis. In particular, the disclosure involves tissue structure formation around a subcutaneously implanted synthetic rod. In addition, the disclosure involves a method for producing said synthetic rod.

28 Claims, 7 Drawing Sheets

(51) Int. Cl.
  *A61L 27/58* (2006.01)
  *A61L 27/18* (2006.01)
  *A61L 27/56* (2006.01)
  *A61L 27/36* (2006.01)
  *A61L 27/50* (2006.01)
(52) U.S. Cl.
  CPC ............... *A61L 27/54* (2013.01); *A61L 27/56* (2013.01); *A61L 27/58* (2013.01); *A61L 2300/414* (2013.01); *A61L 2400/12* (2013.01); *A61L 2430/22* (2013.01); *A61L 2430/34* (2013.01)

(56) References Cited

U.S. PATENT DOCUMENTS

| | | | | |
|---|---|---|---|---|
| 2011/0303228 | A1* | 12/2011 | Witzmann | A61F 2/0036 128/885 |
| 2012/0128932 | A1 | 5/2012 | Vieth et al. | |

FOREIGN PATENT DOCUMENTS

| | | | |
|---|---|---|---|
| JP | 2007312821 | A | 12/2007 |
| JP | 2008-532640 | A | 8/2008 |
| JP | 2013-526649 | A | 6/2013 |
| WO | 2011/147452 | A1 | 12/2011 |

OTHER PUBLICATIONS

Damanik, F., et al., "Co-Culture in vitro study on surface modified PEOT/PBT rods to mimic foreign body response in vivo", In Journal of Tissue Engineering and Regenerative Medicine, Sep. 3, 2012, vol. 6, (suplement 1), blz. 231, 35 P07. [online], [opgehaald op Jan. 15, 2015], ,http://onlinelibrary.wiley.com/doi/10.1002/term.1586/pdf>.

Rothuizen, T.C. et al., "Subcutaneous implantation of polymer rods for the development of an in vivo tissue engineered blood vessel for hemodialysis vascular access", in JOurnal of Tissue Engineering and Regenerative Medicine, Sep. 3, 2012, vol. 6 (supplement 1) blz. 150, 22P29 [online], [opgehaald op Jan. 15, 2015], , http://onlinelibrary.wiley.com/doi/10.1002/term.1586/pdf>.

Rothuizen, T.C. et al., "Development and evaluation of in vivo engineered vascular grafts in a porcine model", in: 51st ERA-EDTA Congress, May 31-Jun. 3, 2014, Amsterdam, The Netherlands, Nephrology Dialysis Transplantation, vol. 29 (supplement 3): iii246-26, SP527. [online], [opgehaald op Jan. 15, 2015], ,http://ndt.onfordjournals.org/content/29/suppl. 3/iii246.abstract>.

Japanese Office Action for Counterpart Foreign Application—dated May 23, 2017.

Rothuizen, TC, et al, "Subcutaneous implantation of polymer rods for the development of an in vivo tissue engineered blood vessel for hemodialysis vascular access", 2012, p. 150, Journal of Tissue Engineering and Regenerative Medicine.

Chinese Office Action for counterpart foreign application dated Sep. 30, 2017.

Japanese Office Action for counterpart foreign application dated Oct. 3, 2017.

Deschamps, A.A. et al., "In vivo and in vitro degradation of poly(ether ester) block copolymers based on poly (ethylene glycol) and poly(butylene terephthalate)", Biomaterials, 25:247-258, 2004.

Nakayama, Yasuhide, et al., "In Vivo Tissue-Engieered Small-Caliber Arterial Graft Prosthesis Consisting of Autologous Tissue (Biotube)", Cell Transplantation, 13:439-449, 2004.

Thapa, Anil, et al., "Nano-structured polymers enhance bladder smooth muscle cell function", Biomaterials, 24:2915-2926, 2003.

Office Action for counterpart EP Application No. 15 733 557.1-1109, dated Mar. 6, 2018, 3 pages.

Pre-Appeal Report for counterpart Japanese Patent Application No. 2016-573501, drafted on Mar. 29, 2018, 3 pages.

"Polymer Based Systems on Tissue Engineering, Replacement and Regeneration", Proceedings of the NATO Advanced Study Institute, Alvor, Algarve, Portugal, Oct. 15-25, 2000, 3 pages.

Rothuizen, Tonia C., et al., "Development and evaluation of in vivo tissue engineered blood vessels in a porcine model", Biomaterials 75:82-90, 2016.

* cited by examiner

A                                               B

A

B

C

A      B

IN SITU TISSUE ENGINEERING

CROSS-REFERENCE TO RELATED APPLICATIONS

This application is the National Stage of International Application No. PCT/NL2015/050442 filed Jun. 16, 2015, which claims the benefit of Netherlands Application No. NL 2013016, filed Jun. 17, 2014, the contents of which is incorporated by reference herein.

TECHNICAL FIELD

The present disclosure relates to the field of in situ tissue engineering, more particularly in situ tissue engineering with the aim of providing a tissue structure which can be used for example as a blood vessel, ureter and/or as a cannulation site in hemodialysis procedures.

BACKGROUND OF THE DISCLOSURE

In arterial bypass procedures and hemodialysis vascular access, there is a need for vascular grafts. However, autologous vessels are not always available due to previous harvesting or pre-existent vascular disease, and synthetic vessels often have poor patency rates due to infection, stenosis and thrombosis.

Therefore, recent approaches are aimed to provide for a completely biological blood vessel, for example via in vitro methods, with the use of scaffolds that are replaced by host cells and matrix over time, or by means of in situ vascular tissue engineering.

In situ vascular tissue engineering was first proposed in the seventies of the twentieth century, using a so-called Sparks mandrill to generate a tissue capsule that was formed around a porous Dacron mesh (Sparks 1969 Ann Thorac Surg August; 8(2):104-13; Sparks 1970 Ann Surg November; 172(5):787-94). This mandrill was implanted for several months in the muscle. However, the grafts largely failed due to thrombosis and aneurysm formation (Hallin 1975 Ann Surg September; 41(9):550-4; Hallin and Sweetman 1976 Am J Surg August; 132(2):221-3; Roberts and Hopkinson 1977 Nov. 5; 2(6096):1190-1).

Other groups have also studied an in situ tissue engineering approach, but using the peritoneum (Campbell et al 1999 Circ Res December 3; 85(12):1173-8) or the subcutaneous pouch (Sakai et al 2009 J of Biomedical Materials Research Part B: Applied Biomaterials: Vol90B(1): 412-410; Watanabe et al 2011 J of Biomedical Materials Research B: Applied Biomaterials Vol90B(1): 120-126) as bioreactor. However, intraperitoneal implantation and the subsequent harvesting are rather invasive and incur the risk of adhesion formation, possibly hindering successful clinical implementation. Moreover, not all implants become encapsulated (Campbell et al 1999 Circ Res December 3; 85(12):1173-8), creating the necessity to implant several devices. The approach of Sakai and Watanabe also leaves room for optimization of e.g. the implants and the characteristics of the generated tissue.

The present disclosure circumvents and/or solves some of the problems associated with earlier approaches and aims for improved methods for in situ tissue engineering, in particular in situ vascular tissue engineering.

SUMMARY OF THE DISCLOSURE

The present disclosure relates to a different approach where a completely biological tissue engineered blood vessel is rapidly generated in situ using the subcutaneous space of a human or animal body as a bioreactor. The use of the subcutaneous space as bioreactor has the advantage that it is easy accessible and that most components desirable for a tissue engineered blood vessel, such as collagen, elastin, fibroblasts and a large vascular network, are present. Moreover, in some clinical settings, such as hemodialysis vascular access, it is the location where the vascular graft is required.

The concept takes advantage of the foreign body response directed to a synthetic mold, e.g. a cylindrical shaped polymer rod, which will evoke an inflammatory response resulting in the encapsulation of this rod by a tissue structure. This tube-shaped tissue structure can form the basis for a tissue engineered blood vessel.

The present inventors found that the tissue structure formation around the subcutaneously implanted synthetic rod can be improved by modulating the implant material characteristics, i.e. the type of material, surface modifications, and bioactive coatings. In contrast to most studies which aim to elicit as little tissue response as possible, the present in situ tissue engineering approach aims to deliberately evoke a pronounced tissue response, with specific requirements to cell type, matrix formation, alignment and distribution of the generated tissue.

In addition, the present inventors overcame a problem concerning the fabrication of large diameter rods (e.g. 30-100 mm) with adequate characteristics, made of a poly (ethylene oxide terephthalate)-poly (butylene terephthalate) copolymer, for use in humans or larger animals (>50 kg). A new compression mold principle was designed using a mold cavity consisting of two halves which can be separated to allow undamaged removal of the rods.

DETAILED DESCRIPTION OF THE DISCLOSURE

The present disclosure provides for a device which is (at least partially or wholly) in the form of a rod having a diameter of 3-20 mm, wherein the surface of the device comprises slowly or non-biodegradable material capable of eliciting a foreign body response, such as at least 0.5, 5, 10, or 20 wt % as compared to the weight of the device. The surface of the outer layer, i.e. the (outer) surface of the device has a root mean square roughness (Rq) of at least 100 nm, preferably at least 125 nm, more preferably at least 150 nm. It is not ruled out that the Rq may be at most 300, 500, 1000, 2000, 5000 nm or even more.

As will be clear, the surface material should not be degraded rapidly, and be able to elicit a foreign body response when inserted subcutaneously in a human or animal body, i.e. the device will be encapsulated by a tissue structure following subcutaneous insertion of the device in a human or animal body within for example 6 weeks. In the present disclosure, slowly or non-biodegradable means that less than 10 wt. % of the material will degrade over time when present in a subcutaneous space of a human or animal body, over a time period of e.g. 6 weeks. Further, the device may consist entirely of the material, or only an outer layer of the device may comprise the slowly or non-biodegradable material. For example, the outer layer may comprise the slowly or non-biodegradable material for at least 50, 70, 80, 90, 95 wt % of the total weight of said outer layer. In the present disclosure, the term "layer" is not intended to mean a section which is necessarily different in composition or otherwise visibly distinguishable from an inner part of the device. The term refers merely to the outer (circumferential) section of the device, e.g. having a thickness of 1-20 mm.

For example, the outer layer may form the entire device, but it is also foreseen that the core of the device is hollow or of a different composition wherein said core is surrounded by the outer layer. In a particular embodiment, the device comprises an inner core (e.g. having a diameter of 1-20 mm) which is more rigid (less flexible) than PEOT/PBT 300/55/45 (described later herein) to reduce the chance that the device breaks during use.

The root mean square roughness (Rq) can be determined through Atomic Force Microscopy (AFM) using e.g. PicoScan Controller 2500-Quadrexed Multimode (Molecular Imaging, USA), with the scan size being (about) 100 µm² (10×10 µm) and using Tapping® Mode. Preferably, images are processed through Nanoscope software (version: 612r1®, 2002 Digital Instrument Veeco) by adjusting different parameters, i.e. integral and proportional gain, to optimize scanning of the surface.

It is clear to the skilled person that roughness analysis can involve measurements of Ra, Rq, and Rmax (Gadelmawla et al 2002; Journal of Materials Processing Technology 123: 133-145). Ra is the most universally used. It is the arithmetic average height parameter, or center line average, and is defined as "the average absolute deviation of the roughness irregularities from the mean line over one sampling length". It averages all peaks and valleys (pores) along the evaluation length, giving a general description of the surface, and neutralizes outlying points. Rq is the root-mean-square roughness parameter corresponding to Ra. It represents "the standard deviation of the distribution of surface heights" and is more sensitive than Ra to large deviations from the mean line:

$$Ra = \frac{1}{n}\sum_{i=1}^{n} |y_i|$$

$$Rq = \sqrt{\frac{1}{n}\sum_{i=1}^{n} y_i^2}$$

Rq can be determined using Scanning Probe Image Processor, SPIP™, version 4.2.2.0 (or later) software, wherein surface roughness of the images can be analyzed, i.e. measured, e.g. by clicking on "Analysis Roughness". As described above, roughness measurements can be performed by 100 µm² surface area. See for more details on Rq measurement Gadelmawla et al 2002; Journal of Materials Processing Technology 123: 133-145.

Furthermore, within the present disclosure, a rod (form) means (substantially) a cylinder (form), wherein the circumference preferably is circle-shaped, although the circumference may also be oval-shaped or have another curved shape. Further, the circumferential shape does not necessarily have to be symmetrical, although this is preferred. The rod (form) may further be bent anywhere along its longitudinal direction (e.g. having an S-shape), and/or the edge of one or both of the longitudinal ends may be rounded such that at least part of the edge (rim) is less angular. In addition, the rod form may comprise a recess (or notch) in one or both end surfaces. It will also be clear that the device as a whole not necessarily has to have a rod form, as long as part of the device has a rod form. Tailor-made rods can be made for each patient having a form (i.e. length and diameter) for the desired application. The diameter of the rod determines the inner diameter of the tissue structure to be obtained. In this way, the tissue structure can be anastomosed to native blood vessel(s) of the patient.

Preferably, the (surface) material capable of eliciting a foreign body response is (or comprises one or more of) a polymer, e.g. a polyester, polycarbonate, poly(orthoester), polyphosphoester, polyanhydride, polyphosphazene, polyhydroxyalkanoate, polyvinylalcohol, polypropylenefumarate, polyterephtalate or a copolymer of one or more thereof; or a copolymer based on polyalkylene oxide and terephthalate, or more preferably a poly(ethylene oxide terephthalate)-poly(butylene terephthalate) copolymer, the latter preferably represented by the formula A/B/C, wherein A, referring to the (average) molecular weight of the initial polyethylene glycol (PEG) used in the copolymer reaction, is between 200-400, preferably between 275-325, more preferably 290-310;

B, referring to the wt. % of poly(ethylene oxide terephthalate) in the copolymer, is 40-70, preferably 50-60, more preferably 53-57; and C, referring to the wt. % of poly(butylene terephthalate in the copolymer, is 30-60, preferably 40-50, more preferably 43-47.

The most preferred PEOT/PBT block copolymer is 300/55/45 (obtainable from PolyVation B.V., Groningen, The Netherlands). Furthermore, it is preferred that the material does not comprise silicone and/or (poly)acrylate.

The device may have a length of 30-800 mm and/or a diameter of 2-100 or 3-20 mm, preferably a length of 40-300 or 50-150 mm and/or a diameter of 6-10 mm. These dimensions have the advantage that the rendered tissue structure will have dimensions that are similar to dimensions of natural blood vessels in humans.

As described earlier, the outer surface of the device can be adequately described in terms of its roughness (Rq), because the roughness is a determining factor for eliciting the desired foreign body response, with specific cell type composition, matrix formation, alignment and distribution of the generated tissue. However, in addition to the roughness (Rq), the surface (of the outer layer) of the device can further be characterized by its porous structure. Said surface may have a porous structure which can be defined as follows:

the pore density is 10-80, preferably 20-60, more preferably 25-50 pores per 100 µm², even more preferably 35-45 pores per 100 µm²;

the average pore diameter is 0.4-1.8 µm, preferably 0.6-1.3 µm, more preferably 0.8-1.0 µm, even more preferably 0.85-0.95 µm.

The pore density can be determined by taking the average number of pores (tiny valleys/holes in the surface) in (at least) nine randomly selected sections of 25000 µm² (magnification 500×) of the respective surface, as determined on the basis of Scanning Electron Microscope images (e.g. using a Philips XL30 ESEM-FEG SEM). Preferably, pores are counted having a diameter of at least 0.025 µm².

Similarly, the average pore diameter can be determined by taking the average of the diameters of all pores to be found in (at least) nine randomly selected sections of 25000 µm² (magnification 500×) of the respective surface (e.g. by SEM). For both pore density and diameter, images can be analyzed with ImageJ 1.46r (or later) to provide the pore size measurements, preferably by applying a threshold, and further inverting the image to allow only the pores to be measured, wherein the scale bar line is used as a reference. Preferably, the average diameter is taken of pores having a diameter of at least 0.025 µm.

In addition, the device according to the present disclosure may have a surface (of the outer layer) which has a wettability characterized by a contact angle of at least 75° according to the captive bubble method, preferably at least 80°, most preferably at least 90°. The captive bubble method is well-known to the skilled person and involves measuring the contact angle between a 2 µL water drop and the surface using drop shape analysis (see Example 2).

As will be evident from the present disclosure, the desired root mean square roughness (Rq), the wettability and/or the pores of the surface (of the outer layer) of the device are obtainable by chemical etching, preferably by exposing the surface of the device, to a halocarbon solvent or an organic solvent such as chloroform and/or dichloromethane, for example by dipping the device in said solvent, in such a way that the desired characteristics are obtained. It will be clear to the skilled person that at least part of the outer surface of the device should have the described Rq, wettability and/or pore structure, and not necessarily the whole surface.

A particularly preferred embodiment according to the present disclosure concerns a device comprising a recess within 30 mm, preferably within 10 mm, of one or both longitudinal ends. Preferably, one or both end surfaces of the device comprise a recess (see for example FIG. 2B). Although such a recess initially occurred as a manufacturing error, it was found that it can advantageously be used to suture the device to the (surrounding) tissue of the subcutaneous space where the device is inserted, in order to avoid migration of the device. As can be seen in Example 1, without suturing the device, it may happen that the device migrates and is no longer in situ any more at the time of harvesting, i.e. no longer within the subcutaneous space where it was inserted.

In other words, the recess can be used to stitch the device such that it stays at the intended place for the intended period. For example, a needle can be inserted into the recess and easily pulled through only part of the diameter of the device, where without the recess said needle would have to be pulled through the entire diameter, or through a section near the rim of the device which may unwantedly damage the device.

Additionally or alternatively, the edge (rim) at one or both longitudinal ends of the device may be rounded, e.g. such that at least part of the edge (rim) is not, or less, angular (see for example FIG. 2A). Of course, rounded in this respect does not refer to a circle or oval-shaped circumferential shape of the edge, but to a rounded transition from one or both end surfaces (bases) of the device to its longitudinal surface. This can be achieved by adapting the rod form of the mold cavity used in the method for producing the device accordingly. It has been found that in this way, the occurrence of decubitus ulcers can be prevented or reduced in patients, and the chance of natural extrusion of the device from the body of the patient can be reduced.

In another preferred embodiment which optionally can be combined with the previous embodiment, the device is bent (following its longitudinal direction) within 50 mm, or preferably within 40, 30 or more preferably within 20 or 10 mm, from one or both longitudinal ends, preferably wherein the device has an S-shape (following the longitudinal direction), meaning that the bends are in (substantially) opposite direction. Of course, this can be achieved by adapting the rod form of the mold cavity used in the method for producing the device. The bend(s) and/or the S-shape will result in a tissue structure with a similar shape which has the advantage that when the tissue structure is used for vascular access in a hemodialysis procedure, it can be more easily and firmly attached to the artery and/or the vein of a patient.

Preparing vascular access is an important step before starting hemodialysis. The vascular access is the site on the body where blood is removed and returned during dialysis, i.e. the cannulation site. To maximize the amount of blood cleansed during the hemodialysis treatment, the vascular access should allow high volumes of blood flow per time unit. This can be accomplished by using the tissue structure according to the present disclosure for connecting an artery to a vein. An S-shaped tissue structure is advantageous, because the rim of both longitudinal ends of the tissue structure can be more easily and firmly attached to the artery and vein, as can be seen in FIG. 10. This prevents that the tissue structure comes loose with respect to the artery and/or the vein.

The device according to the present disclosure may further optionally be at least partially coated with extracellular matrix proteins such as collagen and/or growth factor(s) such as TGF-β, in order to further tune the tissue response when the device is inserted subcutaneously in a human or animal body.

It will be clear to the skilled person that the device according to the present disclosure is suitable for subcutaneous implantation. Preferably, the device does not comprise substances that are toxic, i.e. substances that lead to acute or delayed illness, or of which it is known that they incur an at least 10% increased chance of such illness. At the same time or alternatively, the device is able to elicit a foreign body response when inserted subcutaneously in a human or animal body, i.e. the device will be encapsulated by a tissue structure when the device is inserted subcutaneously in a human or animal body, for example for 1-6 weeks.

Although the present disclosure particularly focuses on the device being (at least partially) in the form of a rod, other forms may also be possible, such as the form of a sheet (e.g. 1, 2, 3, 4, or 5 mm thick), a sphere, or other form such that implantation of the device in the subcutaneous space results in a tissue structure with a desired form, for example a hollow tissue structure that may resemble a patient's (diseased) hollow organ that is to be replaced, for example a blood vessel, ureter, bladder, etc.

The present disclosure also provides for a method for producing the device, in particular a device in the form of a rod which has a specific surface roughness (Rq). The method comprises the following steps:

a) providing a molding apparatus comprising
   a mold cavity which is at least partly in the form of at least one rod having a diameter of 3-20 mm, wherein the rod form is defined by (U-shaped inner surfaces of) at least two mold parts;

b) allowing fluid (e.g. molten, liquid) poly(ethylene oxide terephthalate)-poly(butylene terephthalate) copolymer(s) to fill at least part of the at least one rod form of the mold cavity, optionally by using pressing means;

c) allowing the copolymer to solidify;

d) separating the at least two mold parts from the solidified copolymer to obtain at least one device in the form of a rod having a diameter of 3-20 mm;

e) exposing the at least one obtained device 5-15 seconds to chloroform and/or dichloromethane to obtain at least one device in the form of a rod having a diameter of 3-20 mm, wherein the device comprises a poly(ethylene oxide terephthalate)-poly(butylene terephthalate) copolymer, and wherein the outer surface of the device has a root mean square roughness (Rq) of at least 100 nm, preferably at least 150 nm, even more preferably at least 175 nm, most preferably at least 180 nm.

In step a), a molding apparatus is provided, which can for example be a compression molding apparatus such as the one of Example 3 and FIG. 1. Molding can be seen as shaping a liquid or pliable raw material using a rigid frame called a mold. In line therewith, the present molding apparatus has a mold cavity which at least partly has the form of the product of the method, i.e. at least one rod form having a diameter of 3-20 mm, preferably 4-15 mm, more preferably 6-10 mm.

As can be seen in FIG. 1, the mold cavity can comprise multiple rod formed sub-cavities, such as 1-10, 1-20, or 10-100, or exactly 10 in the example of FIG. 1. These rod-formed sub-cavities may be in connection to a chamber which can be used to provide or store the molding material in, and from where it is subsequently allowed to flow or pressed into the rod-formed sub-cavities, optionally by using pressing means such as a punch that fits into the chamber. By moving the punch within the chamber, which is provided with liquid or moldable molding material, in the direction of the rod formed cavities, said cavities will become filled with molding material.

The at least one rod form of the mold cavity is defined by U-shaped inner surfaces of at least two, preferably exactly two mold parts. In other words, these inner surfaces of said mold parts at least partially follow the circumference of the rod form(s), preferably two mold parts each covering 40-60%, more preferably about 50% of the circumference. The longitudinal ends of the rod need not be defined by an inner surface of a mold part, i.e. the longitudinal end(s) of the rod form may end in (another) subcavity or may be open.

In step b), fluid poly(ethylene oxide terephthalate)-poly(butylene terephthalate) copolymer (PEOT/PBT, obtainable from PolyVation B.V., Groningen, The Netherlands) is allowed to fill at least part of the at least one rod form of the mold cavity. This can be done, for example, by heating the copolymer at least above its melting temperature so as to obtain fluid, moldable copolymer, which is then allowed to fill the at least one rod form of the mold cavity, optionally by using pressing means such as a punch. The use of pressing means has the advantage that the occurrence of air bubbles in the end product is reduced.

Preferably, the poly(ethylene oxide terephthalate)-poly(butylene terephthalate) copolymer is represented by the formula A/B/C, wherein
A, referring to the (average) molecular weight of the initial polyethylene glycol (PEG) used in the copolymer reaction, is between 200-400, preferably between 275-325, more preferably 290-310;
B, referring to the wt. % of poly(ethylene oxide terephthalate) in the copolymer, is 40-70, preferably 50-60, more preferably 53-57; and
C, referring to the wt. % of poly(butylene terephthalate in the copolymer, is 30-60, preferably 40-50, more preferably 43-47.

The most preferred PEOT/PBT block copolymer is 300/55/45 (obtainable from PolyVation B.V., Groningen, The Netherlands).

In step c), the copolymer is allowed to solidify within the mold cavity. This can be done by allowing the copolymer to cool below its melting temperature.

In step d), the at least two mold parts are separated from the solidified copolymer to obtain the at least one device in the form of a rod. It is further preferred that the at least two mold parts are not used to compress the molding material into the mold cavity and/or the at least two mold parts are not separated prior to step d), since this can be done using a punch. The device may be connected to additional solidified copolymer which is not necessarily in the shape of a rod.

The particular advantage of using at least two mold parts each having a U-shaped inner surface forming the at least one rod form is that it allows to remove the at least one device without damaging it. The chance of damaging said device would be greater if the rod formed cavity would be fixed, such that the device can only be removed by pulling or pressing it from one of its ends.

In step e), the at least one obtained device is exposed to a halocarbon or organic solvent, preferably chloroform and/or dichloromethane in such a way and/or for such a period that the desired characteristics (e.g. Rq) are obtained. This can be performed by dipping, immersing or submerging the device in chloroform and/or dichloromethane for the specified period of time. In this way, at least one device in the form of a rod will be obtained having the desired surface characteristics and diameter, wherein the device is capable of eliciting a foreign body response when inserted subcutaneously.

In a preferred embodiment, the device will consist entirely of PEOT/PBT block copolymer, or comprise at least 70, 80, 90, 95 or even 99 wt. % of said material, relative to the total weight of the device. The outer surface of the device, has a root mean square roughness (Rq) of at least 100 nm, preferably at least 125 nm, more preferably at least 150 nm, even more preferably at least 175 nm, most preferably at least 180 nm, and/or at most 300, 1000 or 3000 nm.

The method allows to produce at least one device, e.g. a rod-shaped synthetic mold, which, when inserted for 1-6 weeks in a subcutaneous space of a human or animal body, will evoke a foreign body (or inflammatory) response resulting in the encapsulation of the mold by a tissue structure. This tissue structure can form the basis for a tissue engineered blood vessel.

The present disclosure further provides for a method for providing a tissue structure, wherein the method comprises the steps of
a) inserting the device according to the present disclosure into a subcutaneous space of a human or animal body for a period of 1-6 weeks, preferably 2-4 weeks, to allow a tissue structure to form on the device;
b) preferably removing the device, and optionally the tissue structure formed thereon, from the subcutaneous space. The device and the tissue structure can be separated before or after the removal from the subcutaneous space;
c) preferably, covering the tissue structure with a biodegradable sheet;
d) preferably, connecting the tissue structure to a vein, artery and/or artificial kidney (this step may precede or follow step c)).

For example, in step a), following a small incision of ca. 1 cm, a longitudinal subcutaneous pocket can be formed, for example in the upper extremity (upper arm or forearm), and the device can be inserted into said pocket. The incision can be closed to prevent infection, and only after 1-6 weeks, or 2-4 weeks, access can be made to the subcutaneous pocket, e.g. by making an incision. Then, the device, and optionally any tissue structure formed thereon, can be removed (step b). It is thus a possibility that the tissue structure can remain in the subcutaneous space (in situ) after which one end can be connected to e.g. an artery and the other end to e.g. a vein.

Also provided is the tissue structure obtainable by this method.

Analogously, the present disclosure provides for a substance for use in a treatment of the human or animal body by surgery or therapy, wherein the substance is PEOT/PBT, preferably the PEOT/PBT is 300/55/45, more preferably the substance is (in the form of) a device according to the present disclosure, and wherein the use involves the steps of a) inserting the substance into a subcutaneous space of a human or animal body for a period of 1-6 weeks, preferably 2-4 weeks, to allow a tissue structure to form on the substance;

b) preferably removing the substance, and optionally the tissue structure formed thereon, from the subcutaneous space. The substance and the tissue structure can be separated before or after the removal from the subcutaneous space. Further, steps c), and/or d) as described above may be applied here as well.

The method as described above can result in an (isolated, i.e. outside a human or animal body) tissue structure in the form of a hollow tube characterized in that a 5 μm thick cross section of said tissue structure has the following immuno-histochemical parameters:

15-25% α-smooth muscle actin (α-SMA) positive area relative to total area, as measured by visualizing antibodies against α-SMA (obtainable from Dako, The Netherlands; 1:1000);

90-100% collagen positive area relative to total area, as measured by picrosirus red staining (e.g. Polysciences Inc kit);

and preferably:

0-10% CD45 positive area relative to total area, as measured by visualizing antibodies against CD45 (Immunologic, The Netherlands, 1:50, heat induced 0.1% trypsin antigen retrieval); and/or 0-5% CD68 positive area relative to total area, as measured by visualizing antibodies against CD68 (e.g. AbD, Serotec, clone MAC387, 1:10); and/or 50-70% vimentin positive area relative to total area, as measured by visualizing antibodies against vimentin (Immunologic, The Netherlands; 1:300, heat induced proteinase K antigen retrieval).

The cross section is preferably taken from the middle of the tissue structure, wherein the cross section is transverse to the longitudinal direction. Quantification can be performed using ImageJ image processing and analysis software version 1.33 or later (developed at the National Institutes of Health, US), wherein the percentage of specifically stained area, for example where the visualized antibodies have bound specifically, can be determined relative to the total area of the cross section. It may also suffice to do the quantification based on an image representing at least 10% of the area of said cross section.

The tissue structure may have a composition involving a wall comprising circumferentially aligned αSMA-positive, desmin-negative myofibroblast cells, and circumferentially aligned vimentin-positive, αSMA-negative fibroblasts, and extracellular matrix comprising circumferentially aligned collagen type I and III and glycosaminoglycans, and further comprising any leukocytes and/or foreign body giant cells. The wall thickness may be 0.5-5 mm, or 1-4 mm over at least 80% of the longitudinal length of the tissue structure.

It was found that the tissue structure according to the present disclosure having the above-defined parameters and/or composition has a mean burst pressure of at least 1700 mmHg, preferably at least 2000 mmHg, as determined according to ISO 7198 guidelines (preferably first method therein), which is sufficient for implantation in the arterial circulation. Further, the suture strength as determined according to ISO 7198 guidelines was found to be at least 2.5, preferably at least 3, more preferably at least 3.5 N, and compliance according to ISO 7198 was found at least 5%/100 mmHg, preferably 6%/100 mmHg, more preferably 7.5%/100 mmHg. Without being bound by theory, the present inventors believe it is the (high) level of cross-linking of the collagen in the tissue structure that allows for the high mean burst pressure, and suture strength.

The tissue structure can transdifferentiate into a functional blood vessel, possibly initiated by exposing the tissue structure to blood flow and blood pressure. The tissue structure can thus for example be used as a functional blood vessel and/or as cannulation site for hemodialysis procedures.

It is also envisaged to employ the tissue structure as ureter (tube that leads urine from the kidneys to the bladder) or urethra (tube that leads urine from the bladder to the genitals) It is also foreseen that the tissue structure can be used as conduit between the bladder and the skin surface, for example as aimed for in the Mitrofanoff procedure (Mingin and Baskin 2003, Int Braz J Urol 29 (1): 53-61).

Preferably, the tissue structure is bent within 50 mm, or preferably within 40, 30 or more preferably within 20 mm, from one or both longitudinal ends, preferably wherein the device has an S-shape. This is achieved by using a specifically adapted device that is bent within 50 mm, or preferably within 40, 30 or more preferably within 20 mm, from one or both longitudinal ends, as described earlier herein.

The present disclosure also provides for a tissue structure that is for use (in a treatment of a human or animal body by surgery or therapy) as blood vessel, preferably wherein the blood vessel is for use as cannulation site (i.e. vascular access) for hemodialysis. Also foreseen is the tissue structure that is for use (in a treatment of a human or animal body by surgery or therapy) for implantation as arteriovenous graft. For example, this involves a method of treating a patient in need thereof, comprising implanting, preferably subcutaneously, the tissue structure. A particular advantage may be that the tissue structure is autologous to the patient (donor and recipient are the same). The tissue structure may even already be in situ if the place where the tissue structure is grown is in the vicinity of the place where it is intended for use (e.g. within 10, 8, 5, 2 cm or less). This may be done e.g. in order to replace a diseased blood vessel, such as in an arterial bypass procedure, or to create a cannulation site (i.e. vascular access) for hemodialysis.

It may be advantageous to (at least partially) cover the tissue structure with a biodegradable sheet (e.g. elastic polymer such as polycaprolactone, PCL, less than 3, 2 or 1 mm thick, obtainable from Xeltis). The sheet may have a thickness of 200-800 μm, preferably 300-500 μm. See also FIG. 11. This may give further support to the tissue structure when used in a patient where it is under pressure, so as to further prevent tearing of the structure which may result in bleeding. Use of the sheet may also stimulate elastin formation. In the present disclosure, biodegradable means that the sheet will degrade over time when present in a subcutaneous space of a human or animal body, such that it may disappear over a time period of e.g. 1, 2, or 3 months.

Further, it is envisaged that the tissue structure may be connected to a (wearable) artificial kidney, such as by means of an (artificial or polymer) tube. This may allow hemodialysis outside a hospital, e.g. at home. In addition, it is envisaged that the tissue structure may be connected to a peripheral artery e.g. to create arterial bypass grafts for patients with peripheral arterial obstructive disease, such as in a leg.

The approach according to the present disclosure allows the body to generate its own tissue engineered blood vessels resulting in a less laborious and time consuming process, as for example compared to prior art tissue engineering approach that consists of an in vitro approach wherein a synthetic scaffold seeded with vascular cells is used.

Figure 1:
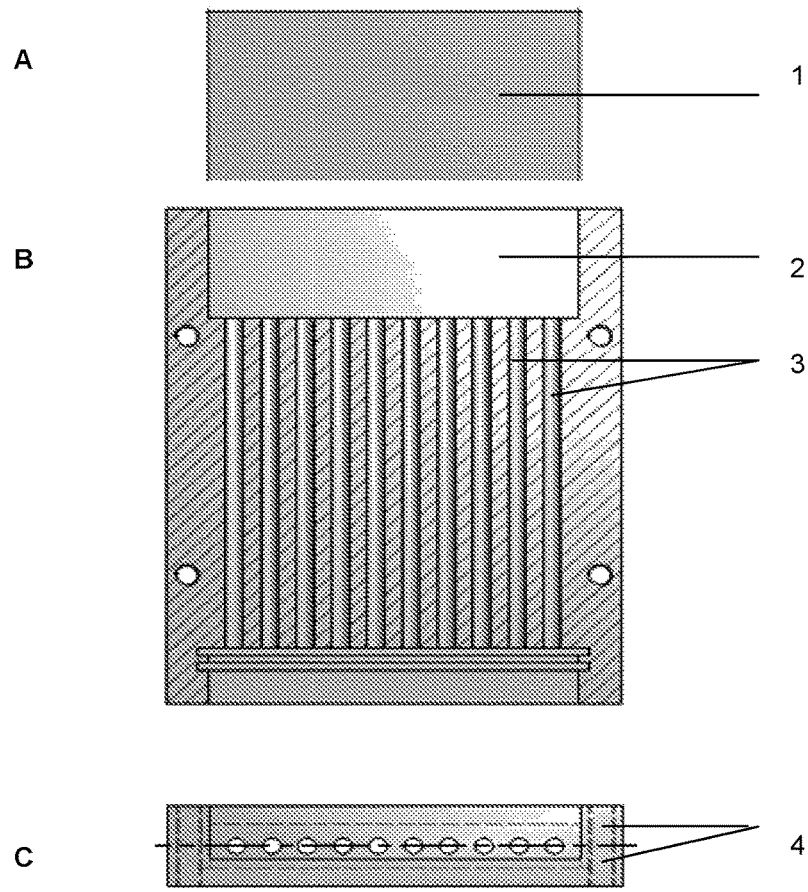
FIG. 1: Transfer molding apparatus comprising a punch (1), a chamber (2); ten mold cavities (3) in the form of rods having a diameter of 8 mm, wherein the rod is defined by the inner surface of two mold halves (4). A: side view; B: top view without the punch showing the middle dotted line representing the border between the two mold halves.
Figure 2:
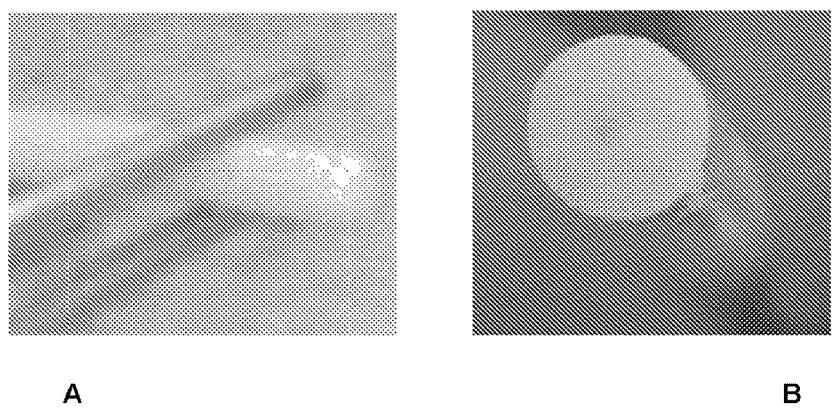
FIG. 2: A: Rod according to the disclosure, having rounded rims (edge) at the longitudinal end. B: Rod having a recess in the surface at a longitudinal end of the rod.

Methods of carrying out the conventional techniques used in methods of the present disclosure will be evident to the skilled person.

EXAMPLE 1

In Situ Vascular Tissue Engineering

This example describes an in situ vascular tissue engineering approach that generates autologous, completely biological tissue engineered blood vessels (TEBVs). Polymer rods were developed that upon implantation evoke an inflammatory response culminating in encapsulation by a tube shaped fibrocellular tissue capsule, which can form the basis for a TEBV. By modulating the implant material characteristics, the tissue response can be tailored to optimize tissue capsule formation. Rods composed of poly (ethylene oxide terephthalate)-poly(butylene terephthalate) (PEOT/PBT) and polyethylene glycol (PCL) and gas plasma treated, chemically etched and growth factor coated rods were implanted subcutaneously in rats and tested on their ability to modify the tissue response. After 3 weeks the rods with the tissue capsules formed around it were harvested and analyzed. Tissue capsules were mainly composed of circumferentially aligned collagen and myofibroblasts. Indeed, different implant material resulted in distinct differences in tissue capsule formation. By varying the implant material characteristics, tissue capsule composition, cell distribution and tissue arrangement could be tailored, thus generating an adequate basis for a TEBV.

Materials and Methods

Fabrication of Rods

Solid cylindrical shaped rods composed of the elastomeric co-polymer poly(ethylene oxide terephthalate)-poly(butylene terephthalate) (PEOT/PBT, IsoTis Orthopedics S.A., The Netherlands) of 1.75 mm diameter and minimal 2 cm length were fabricated with a rapid prototyping unit (Moroni et al 2006 Biomaterials March; 27(7):974-85) (Envisiontec, GmbH, Germany) used as a melt extruder. During fabrication of this co-polymer, ratios PEOT/PBT and the molecular weight of the initial PEG used can be changed, enabling modulation of material properties such as wettability (Deschamps et al 2002 J Control Release January 17; 78(1-3): 175-86) and protein adsorption (Mahmood et al 2004 Exp Cell Res December 10; 301(2):179-88). Briefly, PEOT/PBT granules loaded to a syringe were heated to 180-200° C. A nitrogen gas of 4-5 bars was applied to extrude the melted polymer. Two different compositions of PEOT/PBT were used: a weight % of PEOT/PBT of 55/45 (Polyactive 300®/ Pa300) and 70/30 (Polyactive®1000/Pa1000) with the molecular weight of the initial polyethylene glycol (PEG) used for the copolymer reaction being respectively 300 g/mol and 1000 g/mol. As a control, poly-ε-caprolactone (PCL), well known for its biocompatibility, was used to fabricate rods of similar dimensions using melt extrusion (Axon mini-extruder, Axon AB Plastmaskiner, Sweden). PCL pellets (Purasorb PC 12, Purac Biomaterials, The Netherlands) were heated up to 170° C. and stirred (0.6 cc/revolution) until the PCL was completely melted. Subsequently it was extruded under a pressure of 25 bar through a capillary to fabricate cylindrical rods.

Modification of Implant Material

For chloroform etching, unmodified Pa300 rods were immersed in chloroform (Merck Millipore, The Netherlands) for 10 seconds and vigorously air-dried to let the remaining chloroform evaporate. Rods were then washed in ultrapure water, sonicated twice for 15 minutes at 42 kHz to assure complete removal of the chloroform, and subsequently air-dried. For oxygen gas plasma treatment, unmodified Pa300 rods were treated with 100 mTorr of oxygen gas at either 30 W or 100 W for 5 minutes (Reactive ion etching, Teske, University Twente, The Netherlands). All modified and unmodified rods were sterilized by gamma-radiation (Isotron, The Netherlands) with a dose of >25 kGy. In addition, sterile 100 W oxygen treated Pa300 rods were dipped in a TGF-β solution for 1 minute in a flow cabinet under sterile conditions. TGF-β solution consisted of activated TGF-β3 (R&D Systems, UK) mixed in sterile type I rat collagen (5 mg/mL, Culturex, UK) resulting in a TGF-β concentration of 10 ng/mL collagen. As a control, similar oxygen treated Pa300 rods were dipcoated in type I rat tail collagen without TGF-β for 1 minute. Rods were air dried and directly used for implantation.

Rat Model

Fifteen 13-week old male Wistar rats (Charles Rivers, France) were housed in standard laboratory cages with ad libitum food and water intake. All operations were performed under isoflurane inhalation anaesthesia. Per rat, 4 rods were implanted in the subcutaneous space of the abdominal area. Unmodified PCL rods serving as a control were implanted 5 times and all PA300 and Pa1000 unmodified rods as well as all Pa300 modified and coated rods were implanted 9 times. Following a small horizontal incision of ca. 1 cm, a longitudinal subcutaneous pocket was formed and the rods were inserted in this pocket. Subsequently, the incision was closed using 4-0 vicryl sutures (Johnson & Johnson, The Netherlands). Rats received directly post-operational analgesia via per-operative injection of perfalgan (200 mg/kg). In addition, perfalgan (2.7 mg/mL) was added to the drinking water up to one day after surgery. After three weeks, rods with tissue capsules formed around it were harvested and the animals were sacrificed.

Analysis of Tissue Capsules

Tissue capsules were fixed in 4% paraformaldehyde, processed and embedded in paraffin. Serial cross-sections of 5 μm of two parts of each tissue capsule were made for histological, immunohistochemical and morphometrical analysis. All samples were routinely stained with haematoxylin-phloxine-saffron (HPS). To characterize the extracellular matrix, serial sections of each tissue capsule were stained with picrosirius red for collagen, alcian blue (pH 2.5) for glycosaminoglycans and weighert's elastin for elastin. Sections were stained with alizarin red to assess potential calcification. Elastin was visualised using autofluorescence, excitated with blue light and unmixed with spectral microscopy (Nuance Fx, US). Picrosirius red stained sections were analyzed using both bright field microscopy and with polarized light to discriminate between collagen I and III. All sections of the tissue capsules were compared with similar sections of the medial layer of a native rat aorta. Cellular composition of tissue capsules was characterized using immunohistochemistry, with antibodies against α-smooth muscle actin (α-SMA, Dako, The Netherlands; 1:1000) for myofibroblasts, vimentin (Immunologic, The Netherlands; 1:300, heat induced proteinase K antigen retrieval) for fibroblasts, desmin (Immunologic, The Netherlands; 1:250, heat induced 0.1% trypsin antigen retrieval) for contractile smooth muscle cells, CD45 (Immunologic, The Netherlands, 1:50, heat induced 0.1% trypsin antigen retrieval) for leukocytes, and Von Willebrandfactor (Dako, The Netherlands, 1:300, heat induced 0.1% trypsin antigen retrieval) for endothelial cells and visualised with 3,3'-diaminobenzadine (DAB). Discrimination between fibroblasts, myofibroblasts and contractile smooth muscle cells was made as described elsewhere (Roy-Chaudhury et al 2007 Am J Kidney Dis November; 50(5):782-90). Negative controls were obtained using an isotype antibody. In addition, rods were stained with methylene blue after extrusion from the tissue capsule to determine if any tissue adhered to the rod.

Histomorphometry

Brightfield images of the stained sections were obtained using a panoramic slide scanner (3D Histec, Hungary). Quantifications were performed using ImageJ. Picrosirius red and α-SMA stained sections were used to respectively quantify total collagen area and total myofibroblasts area in $\mu m^2$. The percentage α-SMA positive area was measured using the DAB stained area of the α-SMA stained sections in $\mu m^2$ divided by the total tissue capsule area of a 5 $\mu m^2$ cross-sectional slide.

Statistical Analysis

Data is presented as mean+/−SEM. All data was analysed with an one-way ANOVA test using SPSS. Tukey post-hoc analysis was performed to compare surface roughness grey values of all different rods and histomorphometric results of all unmodified rods with each other. Dunett post hoc analysis was performed to compare histomorphometric results of all modified and coated Pa300 rods with the unmodified Pa300 rods. P-values of <0.05 were considered as statistically significant.

Results

Implant Material

SEM-images confirmed that all unmodified rods had a completely smooth surface, whereas surface modification by oxygen gas plasma treatment and chloroform etching indeed resulted in marked alterations in surface topography, creating distinct homogenously patterned surfaces. Whereas chloroform etching resulted in formation of pores ranging from 0.5-5 μm with some infrequent larger pores ranging from 10-20 μm, oxygen treatment resulted in spiked peaks, with a larger depth for 100 W compared to 30 W oxygen gas plasma treatment. Gamma-radiation did not affect the surface topography (data not shown). Methylene blue staining of the rods after extrusion from the tissue capsule showed that no tissue remained on the unmodified rods, and hardly any tissue on the surface modified and coated rods (data not shown).

General Tissue Capsule Formation

One Pa1000 rod was not in situ any more at time of harvesting. In all other cases, all rods were successfully harvested three weeks after subcutaneous implantation. Rods were completely encapsulated by a well-vascularised tissue capsule, with a more pronounced tissue response at the rims of the rods. Tissue capsules were integrated in the surrounding subcutaneous tissue but could easily be harvested and subsequently smoothly extruded from the rod. Histology revealed that tissue capsules formed around different types of rods discernibly varied in relative proportion of especially collagen and myofibroblast content. Overall, the matrix of the tissue capsules was mainly composed of circumferentially aligned collagen I and III and glycosaminoglycans (GAGs), in composition comparable to a native rat artery. However in contrast to native vessels, elastin was present only locally and in very little amounts. In terms of cellular composition, tissue capsules were dominated by circumferentially aligned α-SMA positive, desmin negative myofibroblasts. The remaining cells were mainly circumferentially aligned vimentin positive, α-SMA negative fibroblasts. The fibroblast/myofibroblast ratio differed between different types of rods. In all tissue capsules, only few desmin positive smooth muscle cells were present. CD45 positive leukocytes were only scarcely present (<1%) and there was no foreign body giant cell formation at the contact surface. Alizarin red staining revealed no signs of calcification in any of the tissue capsules (data not shown). The collagen in the subcutaneous space surrounding the tissue capsules in part co-aligned with the tissue capsule, forming sort of an adventitial layer with loosely arranged collagen, some fibroblasts and small vessels.

Tissue Capsules Formed Around Unmodified Rods

First, three types of unmodified rods were evaluated on their ability to influence the tissue response upon implantation, resulting in significant differences in tissue capsule composition (p<0.05). Whereas the biocompatible PCL rods were encapsulated by a thin-walled, relatively acellular tissue capsule with few myofibroblasts, both Pa1000 and Pa300 rods were encapsulated by a thicker, cell-rich tissue capsule mainly composed of myofibroblasts. Absolute myofibroblast area as well as percentage of myofibroblasts were significantly larger in tissue capsules formed around Pa300 (resp. p=0.048 and p=0.006) and Pa1000 (resp. p=0.010 and p=0.013) rods as compared to PCL. There were no apparent differences between tissue capsules that formed around Pa300 and Pa1000 in histology and histomorphometry. However, Pa300 rods had the advantage that they are less fragile during implantation and thus do no not tend to break during harvesting of the tissue capsules which could damage the tissue capsules (Pa300 compared to Pa1000 rods). Surface modifications were therefore performed on rods composed of Pa300.

Tissue Capsule Formation Around Surface Modified Pa300 Rods

Figure 7:
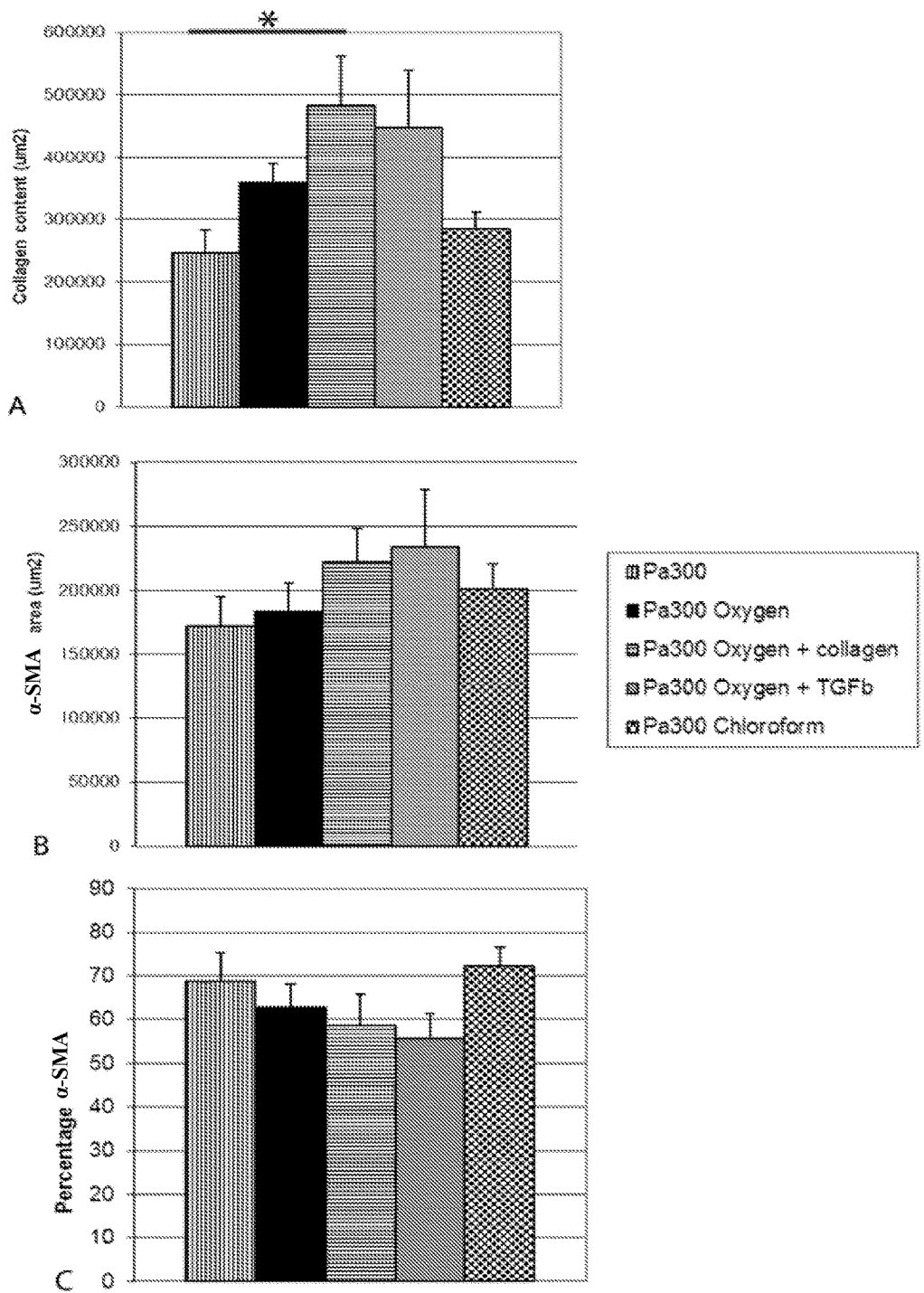
FIG. 7: Quantification of A: the absolute amount of collagen, B: the absolute amount of α-SMA, i.e. myofibroblasts and C: Percentage of α-SMA, i.e. myofibroblasts in tissue capsules formed around modified (Ar 30 min; Ox 5 min; $CHF_3$ 2.5 min; NaOH 10 min; $CHCl_3$ 10 sec) and coated rods in comparison to unmodified Pa300 rods.

Histomorphometry revealed that tissue capsules formed around all modified rods had a larger wall thickness and consequently a larger collagen and myofibroblast content compared to unmodified Pa300 rods. These amounts varied per type of modification of Pa300 rods, as depicted in FIG. 7. Collagen coated rods generated the largest increase of collagen in the tissue capsules (p<0.05), whereas TGF-β coated rods trended towards an increased amount of collagen (p=0.07). Although the absolute amount of α-SMA, i.e. myofibroblasts in the tissue capsules formed around the modified rods increased, the percentage of α-SMA, i.e. myofibroblasts was lower for collagen and TGF-8 coated rods as well as oxygen treated rods as compared their unmodified counterparts. In contrast, chloroform etched rods generated tissue capsules with an increase in the percentage of α-SMA, i.e. myofibroblasts (FIG. 7). As these quantifications do not account for inhomogeneity and morphology of the tissue capsules, tissue capsules were also evaluated on overall appearance and distribution of its content. Marked differences in morphology between different types of rods were observed. Oxygen treated rods yielded tissue capsules with a rather thick wall, yet more loosely arranged. Compared to unmodified rods, both collagen and TGF-β coated rods resulted in thick, densely packed tissue capsules. However the relative proportion of myofibroblasts was lower compared to unmodified rods, with a relative random distribution of myofibroblasts throughout the tissue capsule wall. Chloroform treated rods on the other hand resulted in rather thick tissue capsules, with an evenly distributed wall thickness. In addition, tissue capsules were almost completely composed of densely packed, homogeneously dispersed myofibroblasts.

Using the Foreign Body Response to Generate Tissue Engineered Vascular Constructs The generated tissue capsules were mainly composed of GAGs, circumferentially aligned collagen and myofibroblasts. Even though the evoked response is essentially an inflammatory reaction, there were hardly any leukocytes or foreign body giant cells present in the tissue capsules. Likely, this is dependent on the length of the implantation period. The foreign body response is dynamic, starting with an acute inflammatory phase dominated by neutrophils and macrophages that in weeks resolves in a more fibrotic response with influx of (myo)fibroblasts and matrix formation. In time, a rather acellular collagenous tissue capsule remains. Based on the latter and corresponding with our results, a three-week implant period seems optimal for obtaining a matrix and cell-rich, non-inflammatory tissue capsule in rats.

Modulation of the Foreign Body Response by Altering Implant Material Characteristics The present study clearly indicates that implant properties can favorably impact the tissue response in terms of morphology and composition. Compared to conventional PCL, tissue capsules formed around Pa300 and Pa1000 rods significantly differed in composition. Yet more pronounced differences in both composition and morphology of the tissue were obtained by surface treatment and bioactive coating. We demonstrated that compared to its unmodified counterpart, chloroform etched and oxygen plasma treated surfaces resulted in increased myofibroblast and collagen content of the tissue capsules. Chloroform treatment created a patterned surface with significantly increased roughness. The subsequent differences in implant surface characteristics and topography dictated composition and morphology of the tissue formed around the implant material. Interestingly, the distinct variation in topographical structures and roughness between chloroform etched and oxygen plasma treated surfaces elicited marked difference in tissue arrangement. Although oxygen treated rods resulted in thick tissue capsules, the loose arrangement is not favorable for a vascular construct. In contrast, implantation of chloroform-etched rods resulted in the most homogenously distributed, strong walled, collagen and myofibroblast rich tissue capsule. Therefore, these rods are in our opinion the most favorable to generate an adequate basis for a TEBV.

Modulation of the Foreign Body Response by Bioactive Coating of the Material

In addition to mere surface modification, the modified rods were coated with collagen and collagen/TGF-β. TGF-β induces fibroblasts to myofibroblasts differentiation. Coating of the rods with both collagen alone and collagen/TGF-β resulted in the largest increase in collagen formation and wall thickness compared to unmodified rods. Yet collagen/TGF-β coating did not result in significant different tissue capsules compared to collagen coating alone, suggesting that the result is merely accredited to collagen. Despite the fact that collagen and collagen/TGF-β coated rods resulted in the largest wall thickness, the lower percentage myofibroblasts and their random distribution renders these coatings in our opinion less favourable as bioactive mould for vascular tissue engineering than for example chloroform treated Pa300 rods that generated myofibroblast rich, homogeneous distributed tissue capsules.

Conclusion

Our generated tissue capsules form a basis for a TEBV that might further remodel once grafted into the vasculature. Indeed, myofibroblasts, the main cell type present in the tissue capsules, are plastic cells that possess a contractile apparatus and can synthesize extracellular matrix if stimulated. Importantly, flow and cyclic strain are potent stimuli for matrix synthesis and even myofibroblast to smooth muscle cell differentiation. Thus, upon grafting in the vasculature and exposure to high flow, these tissue capsules might in time differentiate and develop towards a more vessel-like phenotype.

This study illustrates that by exploiting the tissue response directed to a cylindrical polymer rod, a tube shaped basis for a TEBV can be generated. By modifying the implant material characteristics, the tissue response can be tailored, thereby generating an adequate basis for a TEBV.

EXAMPLE 2

Surface Characterization of Rods after Different Surface Treatments

Pa300, Pa1000, and PCL rods were fabricated. Briefly, polymer granules were loaded to a stainless steel syringe and heated at a temperature T=180-200° C. by a thermoset cartridge unit, fixed on the mobile X-axis arm of the apparatus. At the molten phase, a nitrogen gas of 4-5 bars was applied to the syringe via a pressurized cap. Fiber alignment model was loaded on the Bioplotter computer aided manufacturing software (CAM, PrimCAM, Switzerland). A needle outer diameter (OD) of 2.2 mm was chosen to achieve a rod of 1.75 mm. The rods were cleaned with nitrogen gas. Gas plasma rods were incubated in a vacuum chamber. For argon plasma treatment, a Harrick Plasma Cleaner (PDC-002; Harrick Plasma Ithaca, N.Y., USA) was used at 0.133 mbar and High settings (740 V DC, 40 mA DC, 29.6 W) for 30, 45, and 60 minutes, respectively. Oxygen and trifluoromethane treatments were performed with a reactive ion etch (RIE) system (Etch RIE Tetske, Nanolab, University Twente) at 100 mTorr and 30 W for 5, 10, and 15 minutes. Sodium Hydroxide etching was performed at 1 M and 4 M concentrations for 5, 10, and 15 minutes. Rods etched with dichloromethane or chloroform were exposed for 1, 5 or 10 seconds (dipping). After inorganic and organic etching, rods were rinsed once with MilliQ water and further sonicated 2 times for 15 minutes each, to remove remnants.

Atomic Force Microscopy (AFM)—Surface Roughness and 3D Images

To perform AFM analyses, samples were fixed on a magnetic disc with double-side sticky tape. Surface roughness analysis was performed through AFM using Tapping 1 Mode (PicoScan Controller 2500, Molecular Imaging, USA) with a super sharp TESP cantilever: 42 N/m, 320 kHz, 2-5 nm ROC, No Coatings (Bruker AFM Probes.). The roughness measurements (Ra, Rq, and Rmax) were determined using the Scanning Probe Image Processor, SPIP™, version 4.2.2.0 software. Rq measurements were performed by 1 $\mu m^2$ for the nano-scale structures (X, Ar, $O_2$, $CF_3$, and NaOH) and 10 $\mu m^2$ on the microscale structures ($CHCl_3$) surface area. High quality images in three dimensions (3D) of the polymer's surface were recorded and repeated three times at randomly different surface locations to verify the reproducibility of the observed characteristics, and wherein the average was taken.

Contact Angle and X-Ray Photon Spectroscopy

Wettability measurements were done by static water contact angle measurements using the captive bubble method. Measurements were performed using a video-based optical contact angle meter OCA 15 (DataPhysics Instruments GmbH, Filderstadt, Germany). Water contact angle was determined by applying an water bubble (2 μL) on the film using an electronically regulated Hamilton syringe and needle. The contact angle was calculated using SCA20 software (DataPhysics Instruments GmbH, Filderstadt, Germany). Subsequently, the rods were transferred to the XPS chamber. The XPS chamber (Omicron Nanotechnology GmbH) had a base pressure below $1 \times 10^{-10}$ mbar. The measurements were done using a monochromatic Al Kα (XM 1000) X-ray source and an EA 125 electron energy analyzer. All spectra were acquired in the Constant Analyzer Energy (CAE) mode. XPS spectral lines are identified by the shell from which the electron was ejected (1s, 2s, 2p, etc.).

Cell Culture and Proliferation

Neonatal rat dermal fibroblasts (RDFs) purchased from Tebu-bio (R106-05n, Cell Application, Inc.) were cultured with basic culture medium comprising α-MEM (Gibco), 10% fetal bovine serum (Lonza), 2 mM L-glutamine (Gibco) 100 U/ml penicillin and 100 mg/ml streptomycin (Gibco). RDFs were expanded at initial seeding density of 3000 cells/$cm^2$ in basic culture medium and refreshed every 2-3 days. Cells were harvested at 80-90% confluency before trypsinzation for cell seeding. A rat alveolar macrophage cell line NR8383 was obtained from the American Type Culture Collection (ATCC) and maintained in macrophage culture medium, which includes α-MEM without phenol red and addition of L-glutamine (Gibco), 15% fetal bovine serum (Lonza), 100 U/ml penicillin and 100 mg/ml streptomycin (Gibco), with optimum cell seeding density at 200,000 viable cells/ml. Subculturing was done by transfer of medium to another flask. Collection of cells was done by scraping with a Corning® cell scrapers (Sigma-Aldrich, Germany). All cell experiments were performed in a 5% $CO_2$ humid atmosphere at 37° C.

Mono-Culture Cell Seeding of Fibroblasts and Macrophages

Modified and unmodified rods were cut into 1 cm rods per sample and sterilized with 70% ethanol. Rods were pre-incubated for 4 hours in culture medium, comprising α-MEM without phenol red and addition of L-glutamine (Gibco), 10% fetal bovine serum (Lonza), 100 U/ml penicillin and 100 mg/ml streptomycin (Gibco). Agarose molds (3% wt/v) were placed below the rods to prevent cell attachment to 48 well-plates and for optimum static cell seeding. A cell seeding density of 50,000 cells for RDF and 100,000 cells for macrophage was seeded in a 500 μl volume. Samples were rinsed with phosphate buffered saline (PBS, Invitrogen Life Technologies) and collected at day 1 and day 3 for DNA assay, and imaging with methylene blue (MB) and scanning electron microscopy (SEM).

Cell Proliferation Assay

Total DNA was measured with the CyQuant Cell Proliferation Assay kit (Molecular Probes) to access cell adhesion and proliferation. Briefly, culture medium was aspirated and samples were washed gently with PBS. Samples were then collected into a 500 μl eppendorf tube and frozen at −80° C. After freeze-thawing for three times, 250 μl of lysis buffer (1:20 Lysis buffer 20×) were added to the samples at room temperature (RT) for at least 1 hour, and an additional 1 hour with lysis buffer RNase. Subsequently, cell lysate and CyQuant GR dye (1×) were mixed 1:1 in a white 96-well plate and incubated in the dark for 15 minutes. Fluorescence was measured at an excitation and emission wavelengths of 480 and 520 nm, respectively, using a spectrophotometer (The VICTOR3 Multilabel Plate Reader Perkin Elmer Corporation).

Methylene Blue Staining, Immunostaining and Scanning Electron Microscopy

Medium was aspirated from cell culture samples (n=4), cells were washed with PBS and fixed for 30 minutes with freshly prepared 10% formaldehyde in PBS at RT. After rinsing with PBS, samples (n=2) were incubated for 1-2 minutes in 1% Methylene blue solution in PBS and rinsed further with PBS to remove non-specific staining. Samples were examined in an Olympus SZ-III-Stereo Microscopes to see cell distribution on sample. For other fixated samples (n=2), after rinsing with PBS cells were permeabilized with 0.1% Triton X-100 in PBS for 15 minutes in 4° C. and blocked with 1% bovine serum albumin (BSA) for 1 hour at room temperature. Cells were stained with Vincullin-FITC (1:400), Phalloidin-Texas Red (1:100) and Dapi (1:100)

with 3× washing steps in between. Images were obtained by a fluorescence microscope (Nikon Eclipse E600). Afterwards, all stained samples (n=4) underwent dehydration steps of 70-80-90-100%, with an incubation time of 30 minutes per step. After 100%, samples were stored in tissue bag submerged in 100% ethanol and transferred to a critical point dryer chamber (CPD 030 Critical Point Dryer, Leica). At 4° C., 100% ethanol was exchanged with liquid carbon dioxide, which was turned to gas state at 40° C. Carbon dioxide gas was exhausted out at 1 mbar. After all the gas was removed, samples were ready for gold sputtering at a current of 40 mA and a partial pressure of 100 mTorr for 30 seconds. The morphology of the cells was studied using a Philips XL30 ESEM-FEG scanning electron microscope (SEM) at 10 kV and a working distance of 10 mm.

Enzyme-Linked Immunosorbent Assay (ELISA) of TGF-β1, IL-1β, IL-6 and IL-10

Cell culture medium was collected at different points and cytokines secretion of TGF-β1, IL-1β, IL-6 and IL-10 was quantified using an ELISA assay according to the manufacturer's instructions (DuoSet ELISA development kit, R&D Systems Europe Ltd.). Briefly, a 96-well microplate was coated with 100 μL capture antibody per well and incubated overnight at room temperature. Each well was washed with Wash Buffer for three times and block with blocking buffer for a minimum of 1 hour. 100 μL of samples, standard, or controls were incubated for 2 hr at room temperature. A standard curve was prepared according to manufacture standard. The plate was then washed and 100 μL of detection antibody was added and incubated for 2 hr at room temperature. After rinsing, 100 μL of Streptavidin-HRP was added and incubated for 20 min at room temperature. The plate was further washed and 100 μL of Substrate Solution was added for 20 min at room temperature. Finally, 50 μL of the Stop Solution was added to each well. Measurement was performed with a microplate reader at 450 nm and 540 nm wavelength.

Sircol and Fastin Assay for Collagen and Elastin Expression

The amount of elastin and collagen synthesized and deposited on the rods after 4 and 7 days of culture was measured by collagen and elastin staining assay. Samples (n=4) underwent collagen extraction using cold acid pepsin (0.1 mg/ml 0.5 M acetic acid) and left overnight in 4° C. Further collagen isolation and concentration was done before adding the Sircol Dye Reagent. The assay was performed according to the picosirius red-based colorimetric SirCol™ collagen dye binding assay kit (Biocolor Ltd.) and measured at 540 nm with a microplate reader. Rods (n=4) for elastin quantification were firstly heated at 100° C. for 1 hour period with 0.25 M oxalic acid to extract α-elastin. Further elastin quantification was done using a Fastin elastin assay kit (Biocolor Ltd), measured at 513 nm using a microplate reader.

Statistics Analysis

All biochemical assays were performed with triplicate biological sample. Statistical analysis was done by Two-way Analysis of Variance (ANOVA) with Tukey's multiple comparison test (p<0.05), unless otherwise indicated in the figure legends. Error bars indicate standard deviation. For all figures the following applies: *=p<0.05, =p<0.01, *=p<0.001.

Results

Figure 3:
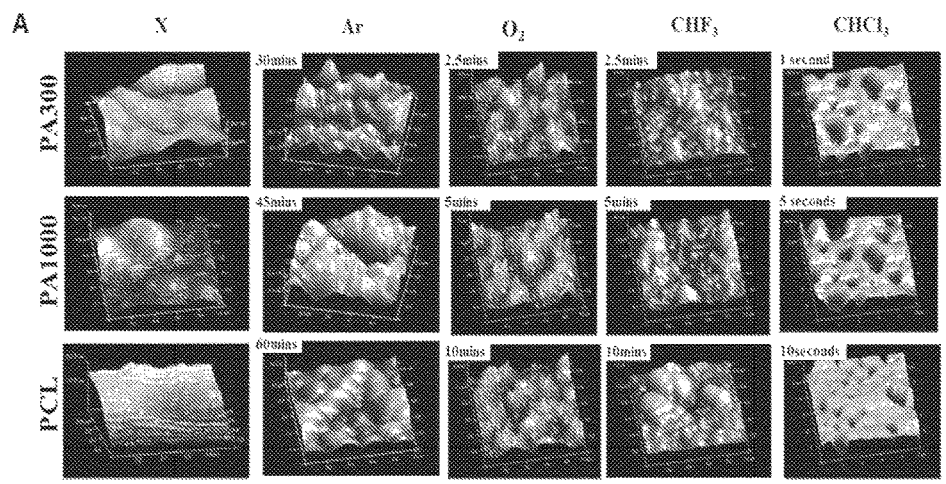
FIG. 3: 3D AFM images of PA300, PA1000 and PCL before and after different surface treatments and exposure time (scan size of 1 $\mu m^2$, with exception to $CHCl_3$ at 25 $\mu m^2$).
Figure 4:
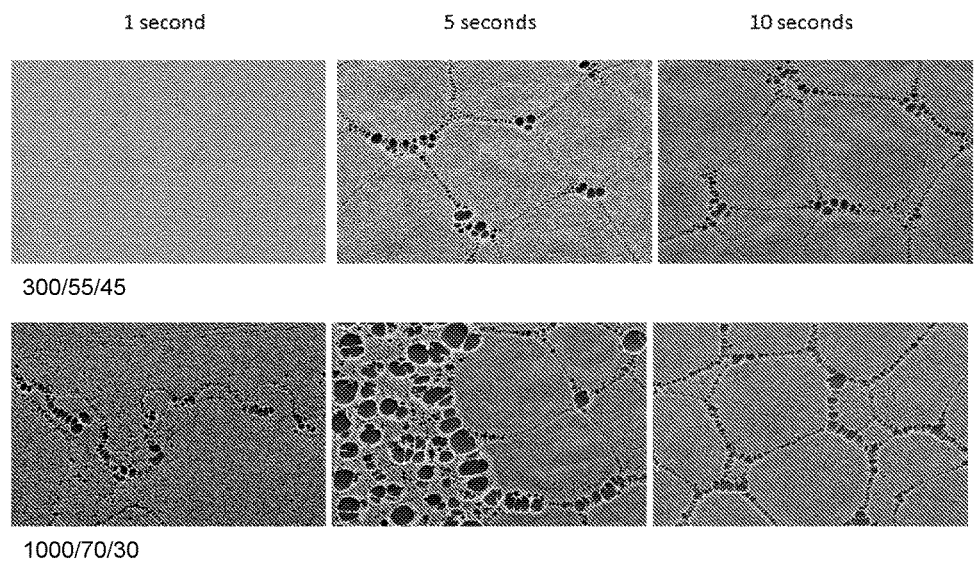
FIG. 4: SEM images of chloroform etched rods after different incubation times (1 s, 5 s, 10 s). Scale: 20 μm (all except top left: 2 μm).
Figure 5:
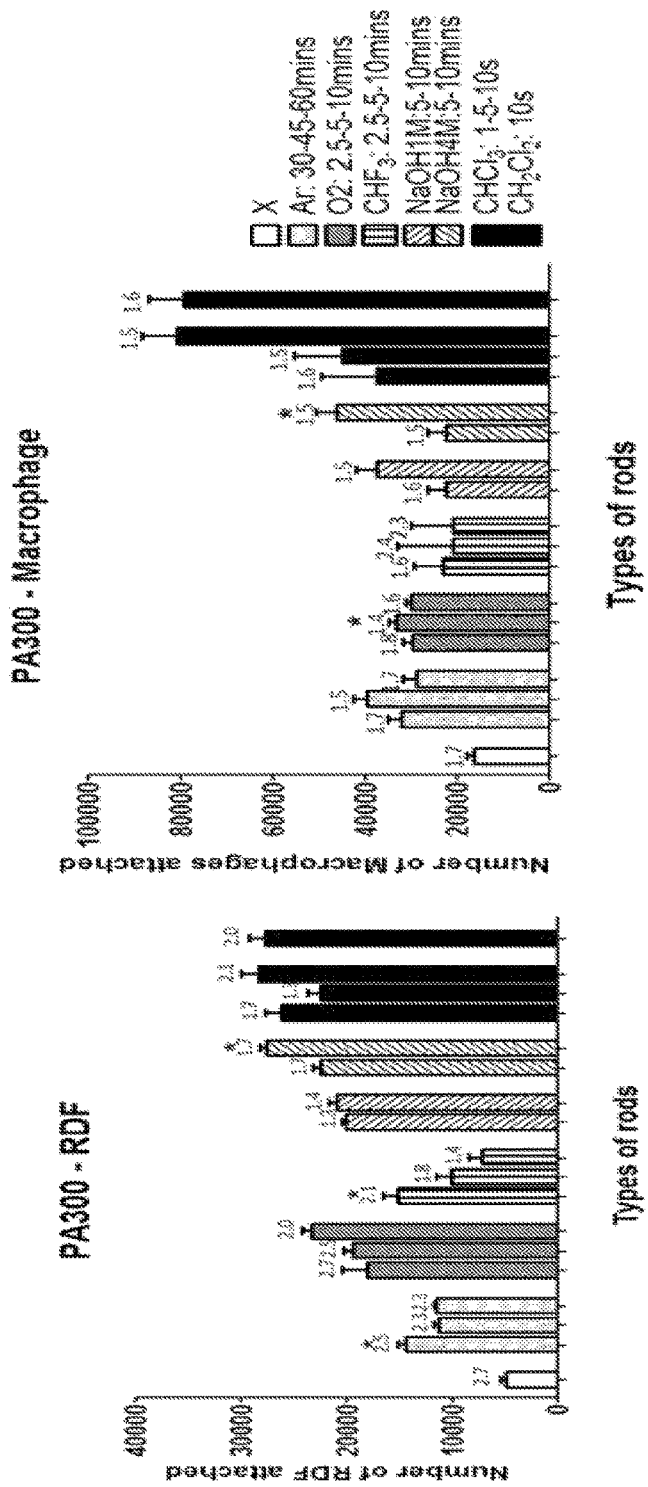
FIG. 5: DNA assay analysis of rat dermal fibroblasts (RDFs, left) and macrophages (right) on attached to PA300 rods which underwent different surface treatment.

As can be seen in FIG. 3: 3D AFM images of PA300, PA1000 and PCL before and after different surface treatments and exposure time (scan size of 1 μm$^2$, with exception to CHCl$_3$ at 25 μm$^2$). FIG. 5: DNA assay analysis of rat dermal fibroblasts (RDFs, left) and macrophages (right) on PA300 at attachment. Unmodified (X) rods were subjected to either argon plasma treatment for 30, 45, and 60 minutes (Ar30-45-60, bars from left to right), oxygen or trifluoromethane plasma treatment for 2.5, 5, 10 minutes (O$_2$2.5-5-10, CHF$_3$2.5-5-10, bars from left to right). Other unmodified rods treated with wet etching using either sodium hydroxide at 1M or 4M concentration for 5 to 10 minutes (NaOH1M:5-10, NaOH4M:5-10, bars from left to right), chloroform or dichloromethane for 1, 5 or 10 seconds (CHCl$_3$:1-5-10 s, CH$_2$Cl$_2$-10 s, bars from left to right). The number of fold increase at day 3 can be seen above individual bars. RDF attachment was statistically increased in all treatments except for CHF$_3$5-10 samples. Macrophage attachment was statistically increased after Ar, Ox and CHCl$_3$ treatments. Star (*, P<0.05) indicates the best parameter for each treatment type. Thus, an increase in cell adhesion was observed in all surface modified rods, with Pa300 showing the most significant increase in comparison to the other polymer types.

Figure 6:
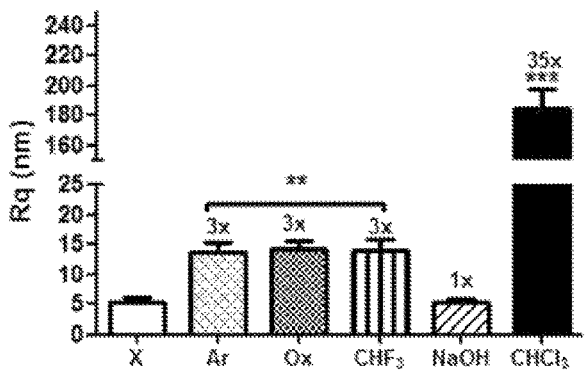
FIG. 6: (a) AFM roughness quantification (Rq at scan size 1 μm) of differently treated rods. The treatment times were as follows: X=unmodified; Ar=argon 30 minutes; Ox=oxygen 5 minutes; $CHF_3$=trifluoromethane 2.5 minutes+NaOH=sodium hydroxide 10 minutes; $CHCl_3$=chloroform 10 seconds. The number of folds each treated rod increase in roughness is shown above its bar. (b) Hydrophilic treatments (70-40°) consisted of Ar, $O_2$ and NaOH, while hydrophobic treatments (85-110°) consisted of $CHF_3$ and $CHCl_3$). (c) Protein absorption assay on unmodified versus pre-selected modified rods.
Figure 6:
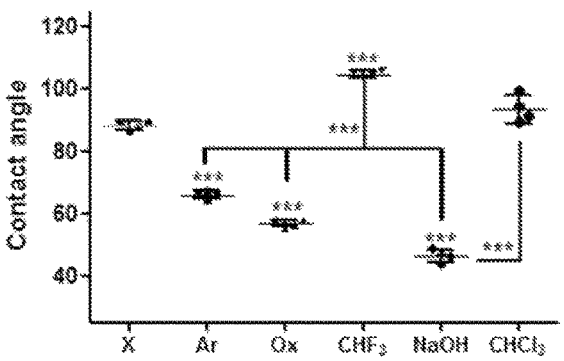
Figure 6:
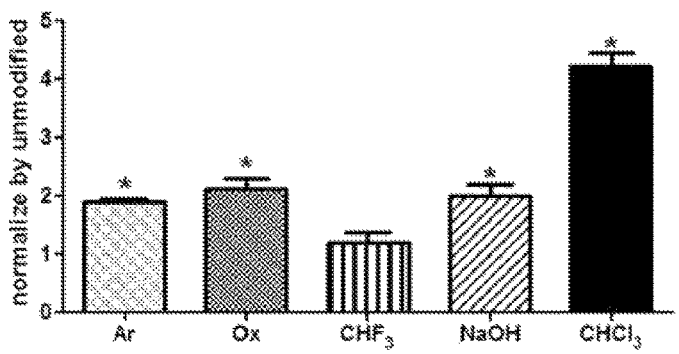

As can be seen in FIG. 6: (a) AFM roughness quantification (Rq at scan size 1 μm). The treatment times were as follows: X=unmodified; Ar=argon 30 minutes; Ox=oxygen 5 minutes; CHF$_3$=trifluoromethane 2.5 minutes+ NaOH=sodium hydroxide 10 minutes; CHCl$_3$=chloroform 10 seconds. The number of folds each treated rod increase in roughness is shown above its bar. (b) Hydrophilic treatments (70-40°) consisted of Ar, 02 and NaOH, while hydrophobic treatments (85-110°) consisted of CHF$_3$ and CHCl$_3$). (c) Protein absorption assay on unmodified versus pre-selected modified rods. Protein absorption in modified rods was normalized by the protein absorption in unmodified rods, thus showing fold differences between the different treatments. Blue stars (*P<0.05, P<0.01, *P<0.001) indicate statistically significant values in comparison to unmodified (X), black stars compares each treatments to one another.

Results further showed that CHCL$_3$ treated rods (10 seconds) provided the highest amount of TGF-β1, IL-β1, IL-6, and IL-10, with the ideal balance to deliver enhanced collagen and elastin secretion, which determines the fate of the tissue generation and functionality. XPS measurement on unmodified versus pre-selected modified rods revealed groups of 2-fold increase (Ar, Ox, NaOH and CHCl$_3$) and 5-fold decrease (CHF$_3$) in oxygen content can be seen.

EXAMPLE 3

A Proof of Concept Study in Pigs

For the pig model, large diameter PEOT/PBT 300 rods (4.2 mm) are needed. Unfortunately, production of these large diameter rods is impossible using rapid prototyping (such as with a Bioplotter device, Envisiontec GmbH). Melt extrusion is also non-favorably because of the undesired macroscopic surface roughness rendered. Compression molding appeared to be the best production method, wherein pellets of polymer are placed in a mold cavity, after which the cavity is closed by a top force and the mold is heated above the melting point of the polymer. The product can then be removed after coiling down of the mold.

For pilot experiments, a single cavity compression mold was used with direct heating, by using two heating clamps, a thermocouple and a control device with temperature set point and readout. Within a short time frame the polymer melted and flowed through the cavity. However, removal of the rods was impossible without damaging the rods due to the high stickiness of the PEOT/PBT material. Therefore, a new compression mold principle was designed using a mold cavity consisting of two halves which can be separated from each other to allow undamaged removal of the rods (see Example 3).

Figure 8:
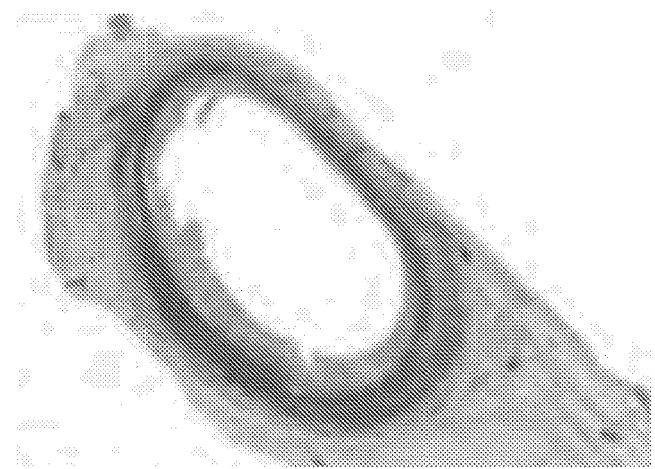
FIG. 8: Subcutaneous implantation of chloroform treated rods in pigs revealed thick tissue capsules that were mainly composed of collagen, myofibroblast en residual inflammatory cells.
Figure 9:
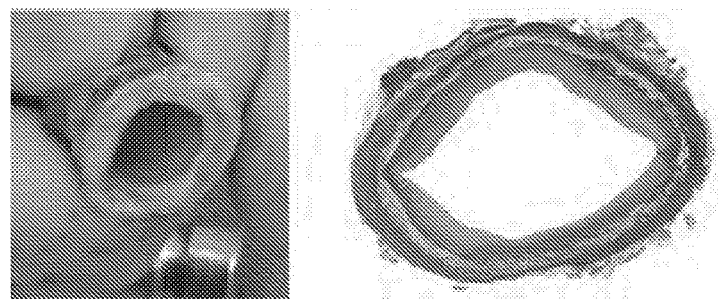
FIG. 9: The tissue capsules of FIG. 8 were implanted as carotid interposition graft in pigs. Four weeks after vascular grafting, 87% of grafts remained patent. At a histological level, the amount of α-SMA positive cells increased substantially as shown in FIG. 9.
Figure 10:
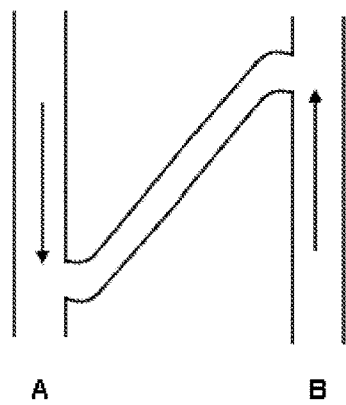
FIG. 10: An S-shaped tissue structure connecting an artery (left, A) and a vein (right, B). The arrows show the direction of blood flow. A cannulated dialysis needle can be inserted into the tissue structure. In a preferred embodiment, the circumference of the (S-shaped) tissue structure can be covered by a biodegradable sheet, e.g. made of PCL.
Figure 11:
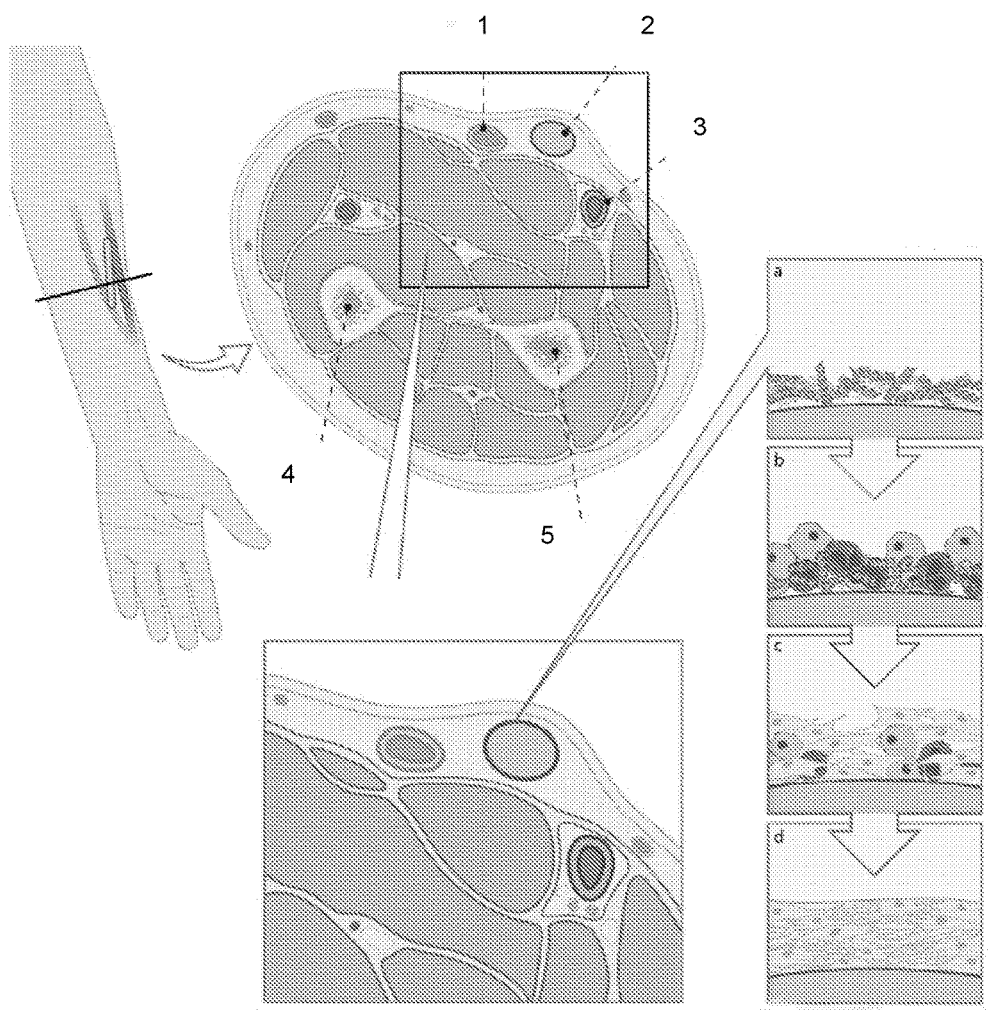
FIG. 11: Device in the form of a rod is placed subcutaneously. Numbers depict: 1. Cephalic vein. 2. Device in the form of a rod. 3. Radial artery. 4. Ulna. 5. Radius. Course of foreign body response: a. protein deposition on the device. b. attachment of granulocytes and macrophages on the device. c. influx of fibroblasts. d. collagen synthesis by fibroblasts and resolution of inflammatory cells.

PA300 rods with Ø 4.2 mm were fabricated as described above. Subsequently, these rods were treated with chloroform for 10 seconds using the same method as for the smaller rods that were implanted in the rats. Subcutaneous implantation of these rods in pigs revealed much thicker tissue capsules that were mainly composed of collagen, myofibroblast en residual inflammatory cells (FIG. 8). Mechanical assessment of these tissue capsules showed a mean burst pressure of >2000 mmHg, sufficient for implantation in the arterial circulation. Next, these tissue capsules were implanted as carotid interposition graft in pigs. Four weeks after vascular grafting, 87% of grafts remained patent. At a histological level, the amount of α-SMA positive cells increased substantially (FIG. 9). Surprisingly, 4 weeks after vascular grafting the tissue capsule wall was largely filled with desmin positive smooth muscle cells. Cannulation studies revealed that mean time to hemostasis after removal of the dialysis needles was <2 minutes.

EXAMPLE 4

Supporting Sheet

External electrospun sheets composed of poly-ε-caprolactone (PCL, Purac Biomaterials, The Netherlands) were fabricated with a fiber thickness of 10±2 μm, a porosity of 90±3% and total thickness of ca. 400 μm. The tensile strength of gamma-sterilised sheets of 440 μm thickness (n=3) was measured using a uniaxial tensile stage (Mecmesin, MultiTest 1-i) equipped with a 50N load cell. Samples were elongated at 10 mm/min and time, displacement and force were recorded. The Young's modulus was determined from the linear part of the stress/strain curve. As reference, samples of ovine pulmonary arteries were measured (n=18). Rods and sheets were sterilised using gamma-radiation of >25 kGy (Synergy Health, The Netherlands). The effect of gamma-radiation on the surface of the chloroform etched rods and the PCL sheets was evaluated using SEM. The tensile strength of the PCL sheet (n=3) was found to be 9 MPa, as compared to 1 MPa of a pulmonary artery. The sheet can be used to support a tissue structure according to the present disclosure by covering the tissue structure with the sheet, i.e. fixing the sheet around the tissue structure.

The invention claimed is:

1. A device configured to provide a tissue structure by eliciting a foreign body response resulting in encapsulation of the device by the tissue structure, wherein the device is at least partially in a form of a rod having a diameter of 2-100 mm, wherein the device comprises a polymer capable of eliciting a foreign body response, and wherein a surface of the device has a root mean square roughness (Rq) of at least 100 nm.

2. The device according to claim 1, wherein the polymer capable of eliciting a foreign body response is chosen from the group consisting of polyester, polycarbonate, poly(orthoester), polyphosphoester, polyanhydride, polyphosphazene, polyhydroxyalkanoate, polyvinylalcohol, polypropylenefumarate, polyterephtalate or a copolymer of one or more of the group or a poly(ethylene oxide terephthalate) poly (butylene terephthalate) copolymer.

3. The device according to claim 2, wherein the polymer has a composition ratio A/B/C, wherein A, a molecular weight of an initial polyethylene glycol (PEG) used in the copolymer reaction, is between 200-400;

B, a wt. % of poly(ethylene oxide terephthalate) in the copolymer, is 40-70; and C, a wt. % of poly(butylene terephthalate) in the copolymer, is 30-60.

4. The device according to claim 3, wherein the molecular weight of the initial polyethylene glycol (PEG) used in the copolymer reaction is between 275-325;

wherein the wt. % of poly(ethylene oxide terephthalate) in the copolymer is 50-60; and wherein the wt. % of poly(butylene terephthalate) in the copolymer, is 40-50.

5. The device according to claim 1, wherein an outer surface of the device has pores.

6. The device according to claim 5, wherein a pore density is 10-100 pores per 100 $\mu m^2$; and/or an average pore diameter is 0.3-2.0 μm.

7. The device according to claim 1, wherein an outer surface of the device has a wettability characterized by a contact angle of at least 75° as measured by captive bubble method.

8. The device according to claim 1, wherein the root mean square roughness (Rq), a wettability, and/or pores are obtainable by chemical etching.

9. The device according to claim 8, wherein the root mean square roughness (Rq), the wettability and/or the pores are obtainable by chemical etching by exposing the surface of the device to a halocarbon or an organic solvent.

10. The device according to claim 9, wherein the halocarbon or an organic solvent is chloroform and/or dichloromethane.

11. The device according to claim 1, wherein the device comprises a recess within 30 mm of one or both longitudinal ends of the device and/or wherein an edge at one or both longitudinal ends of the device is rounded.

12. The device according to claim 1, wherein the device is bent within 50 mm from one or both longitudinal ends of the device.

13. The device according to claim 12, wherein the device has an S-shape.

14. The device according to claim 1, wherein the device is at least partially coated with an extracellular matrix protein and/or a growth factor.

15. The device according to claim 1, wherein the device has a length of 30-800 mm and/or a diameter of 3-20 or 4-15 mm.

16. The device according to claim 15, wherein the device has a length of 50-150 mm and/or a diameter of 6-10 mm.

17. The device according to claim 1, wherein the device is suitable for subcutaneous implantation and/or wherein the device is able to elicit a foreign body response when inserted subcutaneously in a human or animal body.

18. The device according to claim 1, wherein the surface of the device has a root mean square roughness (Rq) of at least 150 nm.

19. The device according to claim 1, wherein the tissue structure forms a basis for a tissue engineered blood vessel.

20. A method for producing a device according to claim 1, wherein the method comprises:

a) providing an apparatus comprising:
   a mold cavity which is at least partly in a form of at least one rod having a diameter of 3-20 mm, wherein the form of at least one rod is defined by U-shaped inner surfaces of at least two mold parts;

b) allowing fluid poly(ethylene oxide terephthalate)-poly (butylene terephthalate) copolymer to fill at least part of the at least one form of the mold cavity;

c) allowing the copolymer to solidify;
d) separating the at least two mold parts from the solidified copolymer to obtain at least one device according to claim 1 in the form of a rod having a diameter of 3-20 mm; and
e) exposing the at least one obtained device for 5-15 seconds to chloroform and/or dichloromethane, wherein the at least one obtained device comprises a poly(ethylene oxide terephthalate)-poly(butylene terephthalate) copolymer, and wherein the surface of the at least one obtained device has a root mean square roughness (Rq) of at least 100 nm.

21. The method for producing a device according to claim 20, wherein the surface of the device has a root mean square roughness (Rq) of at least 150 nm.

22. A method for providing a tissue structure, wherein the method comprises the steps of:

placing a device at least partially in a form of a rod having a diameter of 2-100 mm, wherein the device comprises a polymer capable of eliciting a foreign body response, and wherein a surface of the device has a root mean square roughness (Rq) of at least 100 nm, into a subcutaneous space of a human or animal body to allow a tissue structure to form on the device by eliciting a foreign body response resulting in encapsulation of the device by the tissue structure.

23. The method according to claim 22, wherein the method comprises a further step of covering the tissue structure with a biodegradable sheet.

24. The method according to claim 22, wherein the method comprises a further step of connecting the tissue structure to a vein, artery and/or artificial kidney.

25. The method according to claim 22, wherein the method comprises a further step of employing the tissue structure as a ureter, urethra, or blood vessel.

26. The method according to claim 15, wherein the method comprises a further step of employing the tissue structure as a ureter, urethra, or blood vessel.

27. The method according to claim 26, wherein the blood vessel is for use as a cannulation site for hemodialysis.

28. The method for providing a tissue structure according to claim 22, wherein the method comprises the steps of:

placing the device according to claim 1 into a subcutaneous space of a human or animal body for a period of 2-4 weeks to allow the tissue structure to form on the device.

* * * * *